United States Patent [19]

Niedbala et al.

[11] Patent Number: 5,286,720
[45] Date of Patent: Feb. 15, 1994

[54] COMPOSITIONS AND METHODS FOR TOPICAL TREATMENT OF SKIN LESIONS

[75] Inventors: Raymond S. Niedbala, Wescosville; Elizabeth A. Vail, Bethlehem, both of Pa.

[73] Assignee: Solarcare Technologies Corporation, Bethlehem, Pa.

[21] Appl. No.: 915,142

[22] Filed: Jul. 16, 1992

[51] Int. Cl.$^5$ .................... A61K 31/60; A61K 31/605
[52] U.S. Cl. .................... 514/164; 514/159; 514/722; 514/762
[58] Field of Search ............... 514/164, 159, 722, 762

[56] References Cited

U.S. PATENT DOCUMENTS

| | | | |
|---|---|---|---|
| 4,073,291 | 2/1978 | Marvel et al. | 128/155 |
| 4,224,339 | 9/1980 | Van Scott et al. | 424/289 |
| 4,294,852 | 10/1981 | Wildnauer et al. | 424/317 |
| 4,711,904 | 12/1987 | Luzzi et al. | 514/464 |
| 4,778,786 | 10/1988 | Reever et al. | 514/54 |
| 4,865,028 | 9/1989 | Swart | 606/23 |
| 4,866,095 | 9/1989 | Shroot et al. | 514/569 |
| 4,871,769 | 10/1989 | Fedeli et al. | 514/550 |
| 5,001,156 | 3/1991 | Philippe et al. | 514/555 |
| 5,006,338 | 4/1991 | Luenemann | 424/195.1 |
| 5,017,587 | 5/1991 | Montes | 514/328 |
| 5,045,559 | 9/1991 | Scott | 514/423 |

FOREIGN PATENT DOCUMENTS

| | | |
|---|---|---|
| 1083956 | 8/1980 | Canada . |
| 1280111 | 2/1991 | Canada . |
| 0020029 | 10/1980 | European Pat. Off. . |
| 2302005 | 7/1974 | Fed. Rep. of Germany . |
| 3341881 | 5/1985 | Fed. Rep. of Germany . |
| 2258872 | 8/1975 | France . |
| 274357 | 12/1989 | German Democratic Rep. . |
| 39606 | 1/1980 | Hungary . |
| 40911 | 1/1980 | Hungary . |
| 56-81516 | 5/1982 | Japan . |
| 57-91922 | 6/1982 | Japan . |
| 58-8011 | 1/1983 | Japan . |
| 58-148821 | 9/1983 | Japan . |
| 8500288 | 1/1985 | PCT Int'l Appl. . |
| 96964 | 4/1989 | Romania . |
| 1069834 | 12/1981 | U.S.S.R. . |
| 683743 | 1/1987 | U.S.S.R. . |
| 1537235 | 12/1978 | United Kingdom . |
| 2179858 | 3/1987 | United Kingdom . |
| 2202441 | 9/1988 | United Kingdom . |

OTHER PUBLICATIONS

Chemical Absracts 95:209695m (1981).
Chemical Abstracts 113:84865y (1990).
"Verruca-Freeze" Product Brochure, distributed by CryoSurg, Inc. Jan. 1990.
Michael L. Ramsey, "Plantar Warts-Choosing Treatment for Active Patients," *The Physician and Sportsmedicine*, vol. 20, No. 11, pp. 69-88 (1992).
Copy of page 526 and cover page of "CTFA International Cosmetic Ingredient Dictionary," Fourth Edition. (1991).
Advertisement for OCCLUSAL-HP®, GenDerm Corporation (1991)©.

*Primary Examiner*—Leonard Schenkman
*Attorney, Agent, or Firm*—Panitch Schwarze Jacobs & Nadel

[57] ABSTRACT

Compositions for topical treatment of lesions of human or animal skin which comprise dimethyl ether to freeze the tissue and an acid capable of dissolving the intercellular matrix of the lesion. The dimethyl ether and acid are present in the composition in amounts effective to remove the lesion in a single treatment by a combination of cryogenic and keratolytic action. Methods are provided for the topical treatment of lesions of the skin of human or animal subjects comprising direct spray or intermediate swab application of the present compositions to the lesions.

12 Claims, No Drawings

COMPOSITIONS AND METHODS FOR TOPICAL TREATMENT OF SKIN LESIONS

FIELD OF THE INVENTION

The present invention relates to compositions and methods for topical treatment of various types of dermal lesions of human or animal skin. More specifically, the present invention is directed to compositions and methods having both cryogenic and keratolytic actions for the effective treatment of various lesions on the skin of human or animal subjects.

BACKGROUND OF THE INVENTION

There exist numerous, known conditions which may occur on either human or non-human animal skin that may be expressed as elevations, patches or other types of disfigurement in or on the skin. Some of these conditions are quite contagious and medically troublesome. However, all are cosmetically unacceptable for obvious reasons. Dermal conditions falling within these categories include warts, skin tags, seborrhea keratoses, dermal eruptions caused by papilloma virus, etc.

Effective and safe methods for the treatment of such conditions have long been desired. Some methods and compositions are known to treat such dermal abnormalities, and such compositions may be sold over the counter for direct application to the skin by the patient or are produced for administration solely by physicians.

The most common of the known methods is the treatment of the dermal lesion with an acidic or keratolytic agent. Many of these products are available "over the counter" for application by the patient. Such compositions and methods generally include the use of salicylic acid which has been approved for use in over the counter products by the United States Food and Drug Administration. However, other acids suitable for the treatment of dermal lesions are also known.

For example, U.S. Pat. No. 4,224,339 discloses the use of a composition comprising cysteic acid, homocysteic acid, cysteine sulfinic acid and chelates of these compounds and metallic compounds to treat warts. Other methods employing acidic agents are disclosed in U.S. Pat. Nos. 4,778,786, which is directed to the use of a composition comprising hydroxybenzoic acid; 5,045,559, which is directed to the use of a composition comprising pyroglutamic acid; and 5,001,156, which discloses the use of a composition comprising lipophilic quaternary ammonium salicylate to treat various keratoses. Also, British Patent No. 2,202,441 discloses the topical application of composition comprising citric acid in dimethylsulfoxide to treat warts.

The acidic agents discussed above are used for their keratolytic effect on the lesion. It is believed that the acidic agent acts to dissolve the intercellular matrix in the lesion, causing it to slough off of the skin. With continued and careful treatment, these acidic agents have been found to be generally effective in treating dermal lesions. However, such agents also have shown disadvantages in that they require multiple treatments in order to completely remove the lesion. If the patient does not strictly comply with the multiple treatment regimen, the lesion will frequently repair itself and reappear.

Other known methods for treating skin lesions comprise the application of cryogenic agents to the lesions, a process known as cryotherapy. Unlike acids which act by dissolving the intercellular adhesion within the lesion, it is believed that cryogenic agents act to freeze the water in the tissue of the lesion, thus lysing the cells upon warming. This lysing action effectively kills the cells which are then sloughed off the body as dead tissue.

Cryotherapy is generally practiced only by physicians and cryogenic agents are not available "over the counter." Current cryogenic agents available to the physician utilize liquified gases (such as liquid nitrogen) or fluorinated hydrocarbons (such as FREON®). An example of the use of cryogenic material is disclosed in German Offenlegungsschrift 2 302 005, which is directed to a wart-removing composition which comprises a hydrocarbon or halogenated hydrocarbon coolant, an antibacterial agent and an anti-inflammatory agent. The coolant disclosed for use in the patented composition is difluorodichloromethane. The use of various refrigerants, such as dimethyl ether, alone for the treatment of the skin of a human or animal is disclosed in U.S. Pat. No. 4,865,028.

Although known cryogenic agents reach temperatures effective for cryotherapy, such agents have also demonstrated numerous practical disadvantages. For example, liquid nitrogen readily evaporates and thus requires special storage. Fluorinated hydrocarbons, although effective as cryogenic agents, are known to be deleterious to the environment, particularly the ozone layer. Moreover, most of the known cryogenic agents are chemically and/or physically incompatible with acidic agents, such as salicylic acid. Thus, combinations of these materials have heretofore not been used.

Other known methods for treating skin lesions include procedures to surgically remove the infected tissue. This may be accomplished by simply cutting the tissue with a scalpel or may involve more modern techniques, such as cauterization of the lesion as taught in British Patent No. 1,537,235. Other methods of treatment encompassing surgical procedures include laser treatment, as discussed in French Patent No. 2 258 872, and vacuum treatment, as discussed in German Patent No. 3 341 881. Although effective in removing the treated lesion, such methods are disadvantageous as they cause scarring at the point of surgery.

Also, more recently, other methods for treating skin lesions have become known which comprise the use of pharmaceuticals and chemical agents other than acids, which have heretofore not been used to remove skin lesions. For example, U.S. Pat. No. 4,866,095 discloses the use of adducts of 1,8-dihydroxy-anthrone to treat psoriasis or warts. U.S. Pat. No. 5,017,587 is directed to the use of cycloheximide to heal plantar warts. U.S. Pat. No. 4,711,904 discloses the use of dimethyl isosorbide to treat skin disorders. Antiviral agents have also been proposed for the treatment of warts as disclosed, e.g., in European Patent No. 3 027 758. However, the efficacy of such treatment methods remains in question.

Accordingly, although methods exist which have been relatively effective in treating dermal lesions of humans or animals, each of the known methods has certain disadvantages. Thus, it can be seen that there exists a need for compositions useful for treating lesions on the skin of humans or animals and methods for their use which are efficacious, safe and practical.

SUMMARY OF THE INVENTION

The present invention is directed to compositions for topically treating dermal lesions of human or animal subjects, said compositions having both cryogenic and keratolytic actions and comprising a combination of dimethyl ether and an acid. The present invention is further directed to methods for effectively treating lesions on the skin of human or animal subjects comprising the topical application of the above compositions to the affected area.

DETAILED DESCRIPTION OF THE INVENTION

According to the present invention, compositions having both cryogenic and keratolytic actions are delivered to a lesion present on the skin of a human or animal subject in order to safely and quickly remove the lesion. To provide these actions, the present compositions comprise a combination of a cryogenic agent and an acidic agent providing both cryogenic and keratolytic actions simultaneously in a single application. Thus, the present composition acts to (1) dissolve the intercellular matrix of the lesion (keratolytic action) and (2) freeze the water in the tissue (cryogenic action), simultaneously, causing the lesion to slough off of the body as dead tissue, usually after a single application of the composition.

The preferred cryogenic agent used in the present compositions is dimethyl ether. Dimethyl ether is available commercially as "DYMEL A®" from E. I. du Pont de Nemours & Co., Inc. of Wilmington, Del. Dimethyl ether has been found to be particularly useful in the present composition, since unlike other materials which may have a cryogenic effect, dimethyl ether is physically and chemically compatible with most acids. Thus, a stable combination of dimethyl ether and various acidic agents may be prepared.

The present compositions comprise dimethyl ether in an amount of about 1.0 to about 99% and preferably about 50 to about 95% by weight of the composition.

Other cryogenic compounds may be used in combination with dimethyl ether in order to provide lower freezing temperatures. For example, propane, butane or mixtures thereof may be added to the dimethyl ether for their added cooling.

The present compositions further comprise an acidic agent to provide a keratolytic action on the lesion being treated. The present invention is not limited with regard to a specific acidic agent and any acidic agent which is both physically and chemically compatible with dimethyl ether, provides the necessary keratolytic action (i.e., dissolution of the intercellular matrix) and is dermatologically safe may be used. Acidic agents found to be particularly useful in the present invention include salicylic acid, lactic acid, maleic acid and mixtures thereof. Preferably, salicylic acid is used as the acidic agent of the present compositions.

The present composition should comprise the acidic agent in an amount of about 0.1 to about 30% and preferably about 1 to about 17.5% by weight of the composition.

The present compositions may further comprise various skin conditioning agents and/or solvents which aid in the delivery of the present composition to the skin. The skin conditioning agents help deliver the acid and cryogenic compounds to the skin in a pleasant, non-greasy, or powdery form. These skin conditioning agents act to improve the aesthetic qualities and thus, the consumer appeal of the present compositions. Examples of such skin conditioning agents include glycerin, propylene glycol, monohydric alcohols such as SDA 40 (ethyl alcohol denatured with one or more specific compounds in accordance with regulations set forth in 27 C.F.R. § 21 and oleyl alcohol, polyethylene glycols, water, cosmetic esters or emollients to name a few. Solvents include, for example, ethyl or propyl alcohols and water.

The skin conditioning agents and/or solvents may be used in amounts up to about 5 and preferably about 0.1 to about 2.0% by weight of the composition.

In its presently most preferred form, the present composition comprises about 94.5% by weight of dimethyl ether, 5% by weight of salicylic acid and 0.5% by weight of SDA 40.

In use, the present compositions reach an effective temperature of about $-25°$ to about $-60°$ C., an appropriate range for effective cryotherapy. Preferably, the present compositions reach an effective temperature of about $-40°$ to about $-55°$ C. The effective temperature may be increased or decreased by altering the concentration of dimethyl ether or other cryogenic compounds in the composition accordingly, as will be evident to one skilled in the art based upon the present disclosure.

The present compositions may be prepared by any appropriate method which will be evident to those skilled in the relevant art. However, it is preferred that the present compositions be prepared by first dissolving the acidic agent in alcohol or other appropriate solvent, such as water or SDA 40, in an appropriate aerosol container. Alternatively, the present compositions may be prepared by placing the dry powdered acid directly into the aerosol container with any desired skin conditioning additives. In either case, the valve on the aerosol container should then be sealed. The aerosol container may then be filled with dimethyl ether and optionally other cryogenic compounds to the appropriate pressure level and to the desired concentration. The present compositions may be used with any aerosol container capable of safely storing gases having pressures of up to about 190 psig.

Once prepared in this manner, the present compositions may be sprayed directly upon the lesion being treated. Upon spraying the lesion with the composition, both the acidic agent and the cryogenic agent, i.e., dimethyl ether, are simultaneously provided to the lesion. Preferably, the present composition is delivered to the skin lesions being treated through the use of aerosol containers comprising valves which spray a predetermined dose of the composition onto the lesion.

In the presently most preferred form of the present invention, the present compositions are used with a device such as that disclosed in U.S. Pat. No. 4,865,028. This device comprises a spray can having a shut off valve and a supply tube extending from the valve. A cotton bud is positioned on the end of the supply tube in such a manner that the cotton bud surrounds the outlet of the tube. The cotton bud is completely permeated by the composition when it is discharged from the can. The cotton bud containing the composition is then applied directly to the lesion, providing appropriate quantities of both the dimethyl ether and the acidic agent, thus simultaneously providing cryogenic and keratolytic actions at the site of treatment.

The present compositions may be used to effectively remove lesions present on the skin of human or animal subjects by spraying or otherwise applying an appropriate quantity of the composition directly to the lesion. Appropriate quantities of the present composition to be used for the effective treatment of a specific lesion will vary depending upon a number of factors such as type, size, age and location of the lesion, sensitivity of the patient's skin, etc., as will be evident to one skilled in the art from the present disclosure. It has been found that the present compositions will safely and effectively remove many lesions with a single application. However, the number of applications required to remove a particular lesion from the skin of a particular subject may vary based upon a number of factors, including the type, size, depth and accessibility of the lesion.

The present invention will now be illustrated by reference to the following specific, non-limiting examples.

EXAMPLE 1

Formulation Preparation

Formulation examples are listed in Table I below. The formulations were prepared by initially dissolving the acid(s) and skin conditioning agent in the alcohol and adding a desired amount of the solution to an aerosol container. A valve was sealed onto the container and the cryogenic compound(s) added to the appropriate concentration. Concentrations of the ingredients are in wt/wt %.

TABLE I

| FORMULATION | A | B | C | D | E |
|---|---|---|---|---|---|
| Dimethyl Ether | 48 | 97 | 70 | 49 | 94.5 |
| Propane | 48 | | | 49 | |
| Butane | | | 25 | | |
| Salicylic Acid | 3.5 | 1.0 | 1.0 | 0.25 | 5.0 |
| Lactic Acid | 0.5 | | | 0.25 | |
| Maleic Acid | | | 1.0 | | |
| PEG 540 | | | | 0.5 | |
| Glycerine | | | 1.0 | | |
| Ethanol | | 2.0 | 2.0 | | 0.5 |
| Isopropanol | | | | 1.0 | |

EXAMPLE 2

Comparative Treatments

A formulation containing 95% dimethyl ether and 5% salicylic acid was impregnated onto a cotton wool bud and the solution was applied to a wart present on a human subject. A control human subject having a wart was treated in a similar manner with dimethyl ether only. Within three weeks of the initial treatment, the wart present on the subject treated with the 95% dimethyl ether/5% salicylic acid formulation was completely removed. The control subject wart required four treatments at two-week intervals before it was completely removed.

It is expected that daily treatment with 5% salicylic acid alone would take approximately two to three months to effect complete removal of a skin lesion such as a wart. It is further expected that the use of salicylic acid solutions at two-week intervals would never completely remove a skin lesion such as a wart.

The present invention may be embodied in other specific forms without departing from the spirit or essential attributes thereof and, accordingly, reference should be made to the appended claims, rather than to the foregoing specification, as indicating the scope of the invention.

We claim:

1. A composition for the treatment of warts of human or non-human animal subjects, said composition consisting essentially of salicylic acid and a mixture of dimethyl ether and propane, said mixture of dimethyl ether and propane and said salicylic acid being present in said composition in amounts effective to remove said wart by a combination of cryogenic and keratolytic action.

2. A composition as in claim 1, comprising said dimethyl ether in an amount of about 1.0 to about 99% by weight of the composition.

3. A composition as in claim 2, comprising said dimethyl ether in an amount of about 50 to about 95% by weight of the composition.

4. A composition as in claim 1, comprising said acid in an amount of about 0.1 to about 30% by weight of the composition.

5. A composition as in claim 4, comprising said acid in an amount of about 1 to about 17.5% by weight of the composition.

6. A composition as in claim 1, wherein said composition is capable of producing an effective treatment temperature of about $-25°$ to about $-60°$ C.

7. A composition as in claim 1, further comprising a skin conditioning agent selected from the group consisting of glycerin, propylene glycol, monohydric alcohols, polyethylene glycols, water, cosmetic esters and emollients.

8. A composition as in claim 7, containing said skin conditioning agents in an amount up to about 5% by weight of the composition.

9. A method of treating warts of human or animal subjects comprising applying topically to said wart an effective amount of the composition of claim 1.

10. A method of treating warts of human or non-human animal subjects comprising spraying an effective amount of the composition of claim 1 directly upon said wart.

11. A method of treating warts of human or animal subjects comprising spraying an effective amount of the composition of claim 1 onto a cotton wool bud and applying the wool bud directly to said wart.

12. The composition of claim 1 wherein said salicylic acid is present in an amount of about 5% by weight.

* * * * *